(12) United States Patent
Andersch

(10) Patent No.: US 6,773,381 B2
(45) Date of Patent: Aug. 10, 2004

(54) DEVICE FOR INTERCHANGING SUCTION PIPETTES

(75) Inventor: Walter Andersch, Kirchheim (DE)

(73) Assignee: Siemens Aktiengesellschaft, Munich (DE)

( * ) Notice: Subject to any disclaimer, the term of this patent is extended or adjusted under 35 U.S.C. 154(b) by 520 days.

(21) Appl. No.: 09/908,246

(22) Filed: Jul. 18, 2001

(65) Prior Publication Data
US 2002/0061259 A1 May 23, 2002

(30) Foreign Application Priority Data
Nov. 22, 2000 (DE) ......................................... 100 577 87

(51) Int. Cl.$^7$ ............................................... B23Q 3/155
(52) U.S. Cl. ............................... 483/16; 483/58; 483/59
(58) Field of Search .............................. 483/16, 54, 55, 483/58, 59, 901; 29/743; 211/1.52, 1.55, 89.011

(56) References Cited

U.S. PATENT DOCUMENTS

| | | | | |
|---|---|---|---|---|
| 4,480,780 A | * | 11/1984 | Claeskens et al. | 29/743 |
| 4,868,978 A | * | 9/1989 | Seidel et al. | 29/743 |
| 4,875,285 A | * | 10/1989 | Haan et al. | 29/740 |
| 5,228,732 A | * | 7/1993 | Rauscher | 29/743 |
| 5,287,608 A | * | 2/1994 | Ellis | 29/741 |
| 5,372,568 A | * | 12/1994 | Matsuoka | 483/59 |
| 5,624,364 A | * | 4/1997 | Zimmer | 483/16 |
| 5,655,354 A | * | 8/1997 | Baker et al. | 483/58 |
| 5,688,215 A | * | 11/1997 | Mase et al. | 483/66 |
| 6,428,454 B1 | * | 8/2002 | Yokota et al. | 483/59 |
| 6,568,069 B1 | * | 5/2003 | Melf et al. | 29/743 |

* cited by examiner

Primary Examiner—A. L. Wellington
Assistant Examiner—Dana Ross
(74) Attorney, Agent, or Firm—Baker Botts LLP

(57) ABSTRACT

The invention relates to a device for interchanging suction pipettes which can be removed from a magazine and coupled to a fitting head of a fitting device and detached from the fitting head and deposited in the magazine. The fitting head has, on its side facing the magazine, a motor on whose driven shaft a star-shaped part and a latching plate are mounted. The latching plate has at least one nub (121) which, after insertion of the star-shaped part into a star-shaped cutout in the suction pipette held in the magazine and after rotation of the star-shaped part and the latching plate into a locking position, engages in a notch, and which, on insertion of a suction pipette held on the star-shaped part into the magazine, can be moved out of the notch. The magazine has, on the side facing the fitting head, a sliding ring which is arranged in a rotationally fixed manner in the magazine and into which the suction pipette can be inserted in such a manner that the star-shaped latching plate comes to rest with its outer edges on the sliding ring where it is raised resiliently away from the star-shaped part, so that the nub is situated above that surface of the suction pipette which faces the fitting head.

12 Claims, 3 Drawing Sheets

DEVICE FOR INTERCHANGING SUCTION PIPETTES

FIELD OF THE INVENTION

The present invention relates to a device for interchanging suction pipettes which can be removed from a magazine and coupled to a fitting head for the automatic fitting of printed circuit boards with component.

BACKGROUND OF THE INVENTION

It is known to couple suction pipettes onto a fitting head for the automatic fitting of components on printed circuit boards, after removal from a magazine, and return them to the magazine from the fitting head after a fitting operation. The pipettes provided in the magazine are usually received by a sleeve having a star-shaped part that is connected by rotation in an interlocking manner to the intersecting point of the pipette and secured by a latching plate. This process is explained in greater detail in conjunction with FIG. 1 in which a fitting head 3; a rotary motor for the fitting head 3; a star-shaped latching plate 12; and a star-shaped part 4 arranged so as to be aligned with respect to each other on the drive shaft of the rotary motor 14. During the coupling of the pipette, the star-shaped part, which has a longitudinal passage 18, is inserted by exerting a pressure in the direction of the pipette (Z axis) into a star-shaped cutout in the pipette held in a magazine. The star-shaped cutout is situated on the surface of the pipette which faces the fitting head. By rotation of the star-shaped part 4 in the direction of the pipette while held firmly in the magazine, the star-shaped part 4 is locked in a bayonet-like manner to the pipette, where by the outer edges of the projection of the star-shaped part pass under the star-shaped cutout in the circumferential direction. This corresponds to the locking position between the star-shaped part 4 and the pipette. A star-shaped, resilient latching plate is fastened congruently to the star-shaped part 4 and has a projection or a nub which faces the pipette. On rotation of the star-shaped part 4 together with the latching plate into the locking position, the nub slides over an arc of a circle outside the star-shaped cutout of the pipette until it enters the locking position, i.e. a notch which is situated on the arc of the circle. This has the effect of maintaining the locking position. An annular seal, which is provided on the star-shaped part ensures a tight connection between the above-mentioned hole in the star-shaped part 4 and the pipette, so that a vacuum can be applied to the pipette via the hole in the star-shaped part 4.

One problem with such a locking arrangement, i.e., between the star-shaped part and the pipette, is that a relatively large force is required for detaching the star-shaped part from the pipette because of the latching force of the nub of the latching plate. This is so, even if the notch in the arc of the circle has sloping surfaces. Thus, the force or moment required for rotating the star-shaped part in relation to the pipette therefore has to be relatively large. Conversely, if a certain, minimum moment is specified, the retaining force is defined by this moment. A further disadvantage is that the wear on the notch and nub is relatively great, and so the useful life of the pipettes is limited.

SUMMARY OF THE INVENTION

The object of the present invention is to provide a device, whereby the interchange of suction pipettes on a fitting head can be carried out reliably with comparatively small coupling and uncoupling moments. An important aspect of the present invention which enables this object to be realized is the fact that a relatively small moment is sufficient for rotating the star-shaped part into the locking position when a pipette is picked up out of a magazine, since unlike the prior art, the latching plate does not directly engage the pipette itself, but rather a special sliding ring having a low coefficient of friction. Accordingly, during the latching and unlatching process, the nub of the star-shaped latching plate does not have to overcome sides of the notch of the pipette. Because the nub slides on the sliding ring which has a small coefficient of friction, after the locking position is reached and the latching plate is relieved of load, the nub is gently inserted into the notch in the Z axis from above from the sliding ring. Conversely, on insertion of the pipette into a magazine and with the latching plate being pressed down, the nub is moved upward in the Z axis out of the notch because the latching plate comes to rest on the sliding ring. As a result, the moments occurring during the latching and unlatching of the nub can advantageously be reduced by up to a factor of six (6) and there is no wear in the region of the notch. In a preferred embodiment of the present invention, the retaining force between the pipette and star-shaped part is increased by prestressing of the latching plate.

The low coupling and uncoupling moments enable a motor which is less powerful in terms of torque and therefore lighter in weight to be used. This is of importance since the star-shaped part and latching plate and the pipette connected thereto in the locking position fit directly on the shaft of the motor, and hence the motor can be accelerated directly in the direction of the Z axis during the fitting process. When placing components on a printed circuit board using relatively low attaching forces, the weight of the motor must also be low. By means of the present invention, an attaching force of, for example, 0.5 N, which is the lowest which is required, can be achieved with a relatively high fitting speed. Further, the novel device may be designed in such a manner that it can also be used in conjunction with presently known pipettes and a new design for the pipettes is not required.

BRIEF DESCRIPTION OF THE DRAWINGS

The present invention is described below in more detail, and in conjunction with the figures, in which.

DETAILED DESCRIPTION OF THE INVENTION

Figure 1:
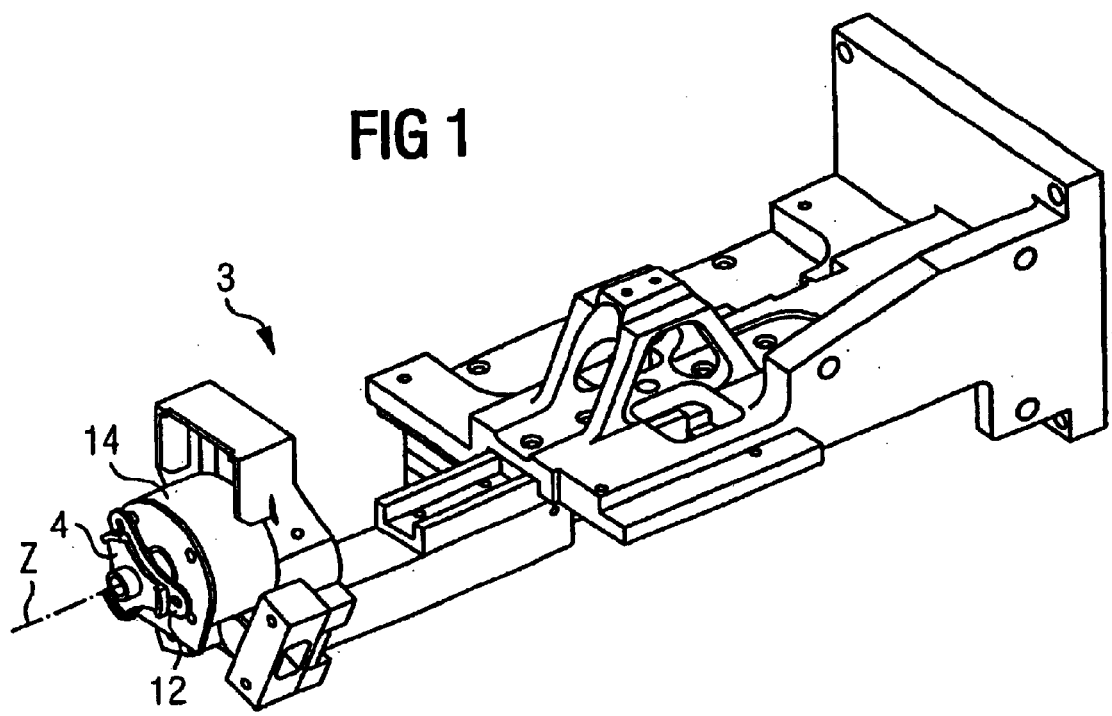
FIG. 1 is a perspective illustration of a known fitting head having means for interchanging suction pipettes.
Figure 2:
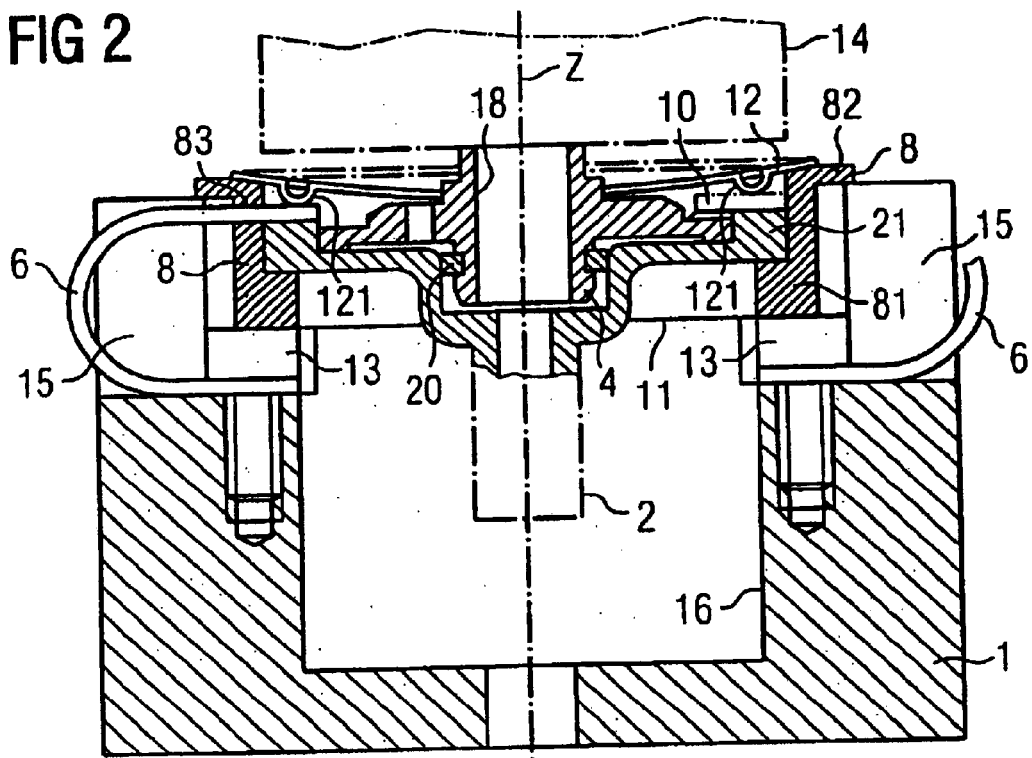
FIG. 2 is a section through the device according to the present invention, with the star-shaped part being arranged in the locking position.

In FIG. 2, a pipette 2 is arranged in a magazine. A sliding ring 8 is also arranged in the magazine 1, and into which the pipette 2 can be inserted. The sliding ring 8 preferably has a lower, radially inwardly protruding flange 81 on which the outer edge 21 of the pipette 2 rests. The sliding ring 8 further preferably has an upper, radially outwardly protruding flange 82 which rests on the upper side of the magazine 1. The magazine 1 expediently has the shape of a square housing with a space 16 which serves to accommodate the lower region of the pipette 2. The interior space 16 widens outward via a step 11 on which the lower flange 81 and the sliding ring 8 rests. A retaining spring 6 is arranged in two radial incisions 15 provided on opposite sides of the magazine 1. The retaining spring has a substantially U-shape design with a lower leg portion being fastened by a screw 13 below the step 11 of the bottom of the incision 15. Starting from the lower leg which runs radially outward in the incision 15, the retaining spring 6 runs in a curved manner to an upper leg which runs radially inwardly in the incision 15, the free end region of which is guided through a radial cutout 83 in the sliding ring 8. As it does so, the retaining spring 6 uses its spring force to pull the sliding ring 8 in the direction of the step 11.

Figure 3:
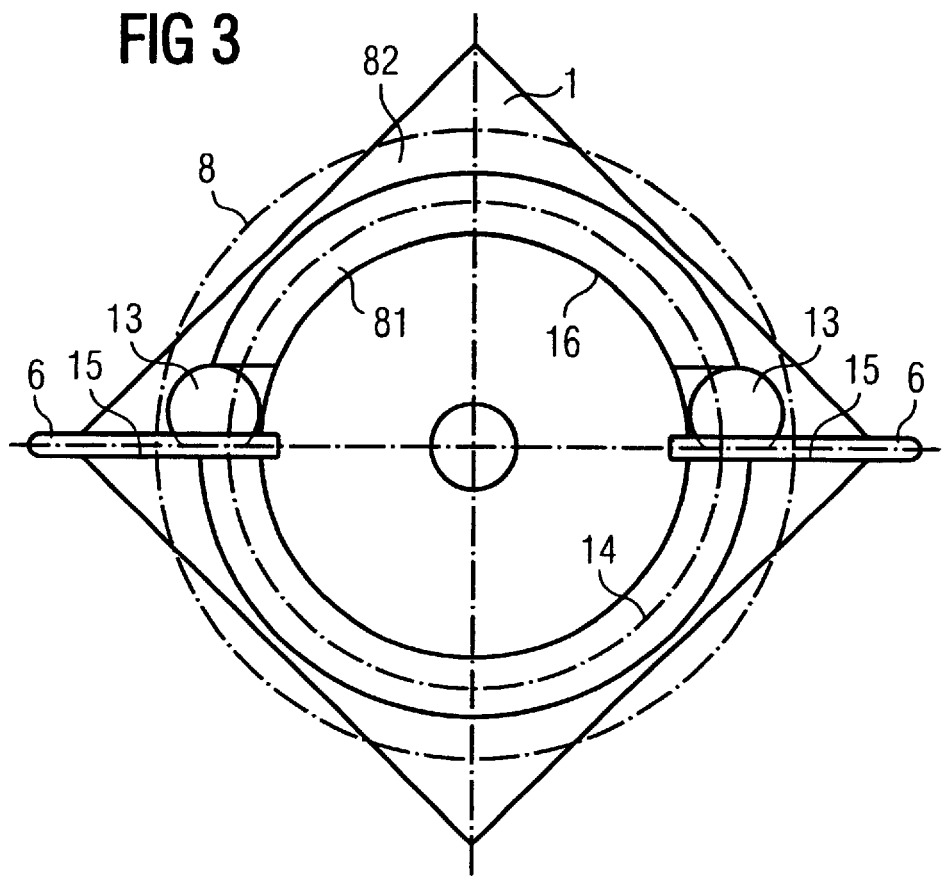
FIG. 3 is a plan view of the device shown in FIG. 2 from above a magazine.
Figure 4:
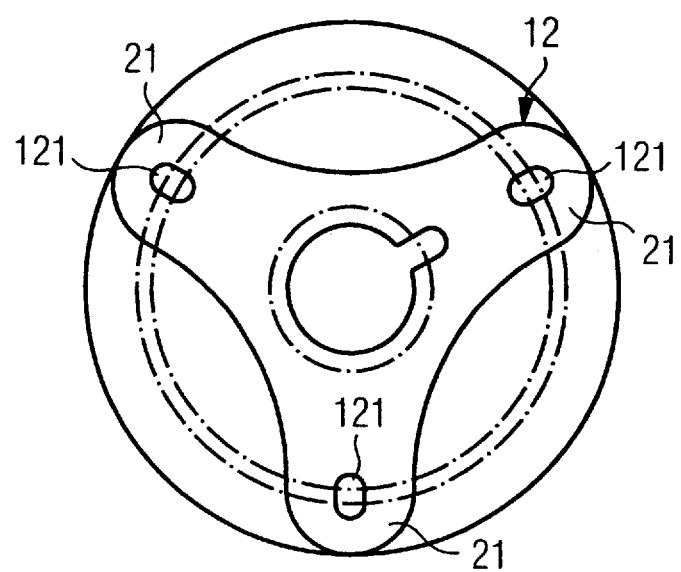
FIG. 4 is a plan view from above of the latching plate fitting on the sliding ring.
Figure 5:
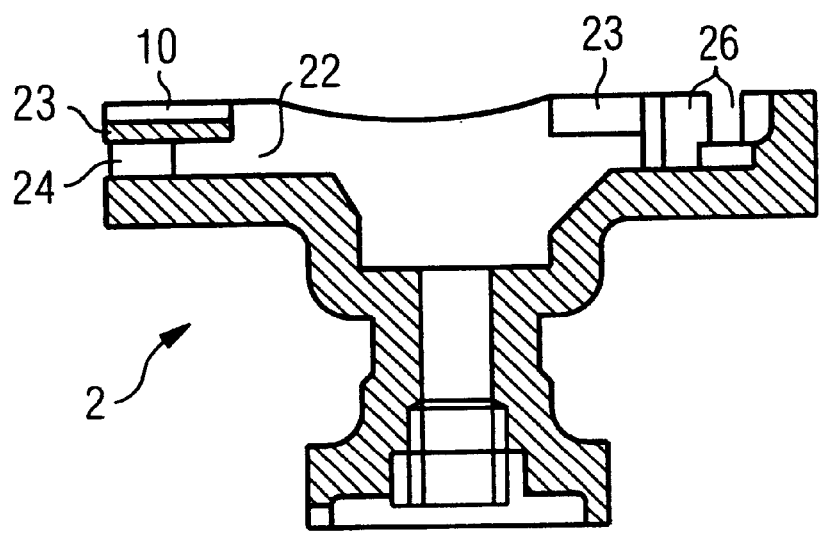
FIG. 5 is a section through a pipette.
Figure 6:
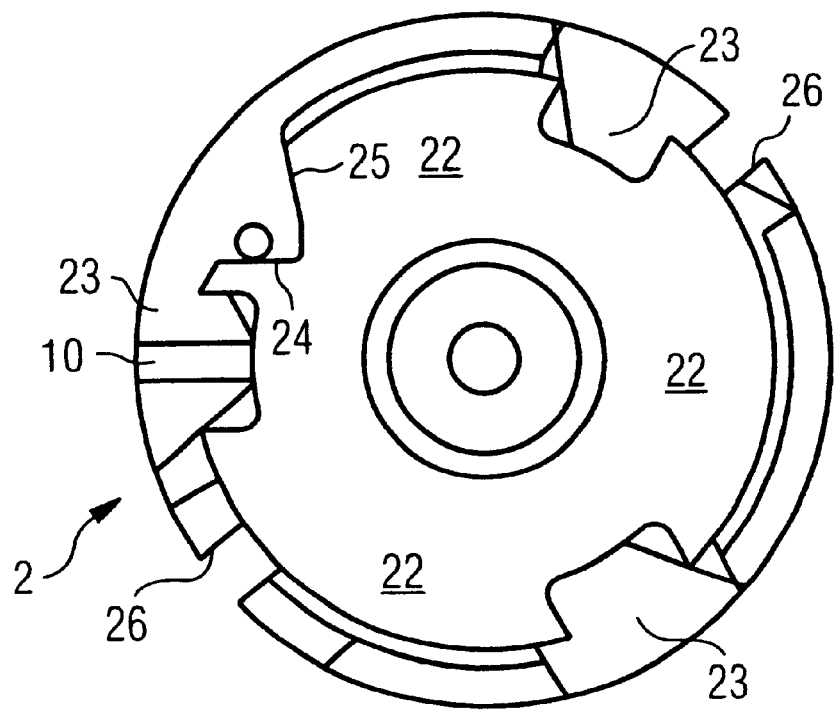
FIG. 6 is shows a view of the pipette from the fitting head.

In FIG. 3, the sliding ring 8 and the flanges 81, 82 are illustrated as seen from above by dash-dotted lines. The star-shaped latching plate 12, which preferably consists of spring steel, has nub 121 on a projection protruding outwardly in a star-shaped manner. The nub 121 protrudes in the direction of the sliding ring 8 and, in a locking position, latches into the notch 10 which is situated on the surface of the pipette 2 which faces the latching plate 12. The view of the pipette 2 from a motor 14 is illustrated in FIG. 6. FIG. 5 shows a section through the pipette 2. The star-shaped cutout for accommodating the star-shaped part 4 is denoted by 22 and the wall parts are denoted by 23. The radially extending notch 10 is situated in one wall part 23 (in the left-hand wall part 23 in FIGS. 5 and 6), on the side which faces the star-shaped part 4. Situated on the rear sides of a wall part 23, as seen in the rotational direction of the locking position, is a stop 24 for the corresponding edge of the projections of the star-shaped part 4 for securing the locking position.

In order for the pipette 2 to be inserted into the sliding ring 8 and removed therefrom, incisions 26 are formed opposite each other on the outside, and through which the ends of the upper legs of the retaining springs 6, which protrude radially inward by over the sliding ring 4, can pass upon insertion and removal of the pipette 2 into the sliding ring 4.

The latching plate 12 is dimensioned in such a manner that it protrudes outwardly over the circumference of a pipette 2 which is to be picked up. Therefore, on entry of the star-shaped part 4 into the star-shaped recess 22, latching plate 12 comes to rest on the upper flange 82 of the sliding ring 8 and is raised in the Z axis counter to its spring force sufficiently for the nub 121 to be situated above the plane of that surface of the pipette 2 in which the notch 10 is arranged. This has the effect that when the star-shaped part 4 and the latching plate 12 are rotated (in the clockwise direction in FIG. 6), the latching plate 12 slides with its outer edges 21 on the sliding ring 8 until the nub 121 is situated in the locking position above the notch 10. When the sleeve 2 and the star-shaped part 4 are raised, the resiliently prestressed latching plate 12 relaxes and the nub 121 enters from above in the Z axis into the notch 10.

In order to enable a particularly friction-free rotation of the latching plate 12 on the sliding ring, the sliding ring 8 is preferably manufactured from a readily slideable plastic material which has a very low coefficient of friction. As an alternative or in addition, the latching plate 12 can be coated with a material of a small coefficient of friction at least in its regions which rest on the sliding ring 8. A low moment (force) is therefore sufficient for rotating the star-shaped part 4 and the latching plate 12, since the latching plate 12, unlike in the prior art does not slide on the pipette itself, but rather slides on the sliding ring 8 which has a relatively low coefficient of friction. Since the nub, 121 executes a vertical movement during the latching and unlatching process, it does not have to overcome the slopes of the notch, as is required in the prior art.

When the pipette 2 is deposited in the sliding ring 8 of the magazine 1 (in which case the free ends of the upper legs of the retaining springs 6 enter into the incisions 26), the latching plate 12 again comes to rest on the flange 82 of the sliding ring 8, and in the process the nub 121 is raised upward in the Z axis out of the notch 10, and the latching plate 12 is prestressed counter to its spring force. During subsequent rotation of the star-shaped part 4 and the latching plate 12 out of the locking position (rotation in FIG. 6 anticlockwise), the latching plate again slides with low friction on the sliding ring 8 until the star-shaped part 4 passes out of the region of the wall parts 23 and moves away from the magazine 1 in the direction of the Z axis, when the ends of the upper legs of the retaining springs 6 are aligned with respect to the incisions 26.

What is claimed is:

1. A device for interchanging suction pipettes which are to be removed from a magazine and coupled to a fitting head of a fitting device and detached therefrom and deposited in the magazine, the fitting head comprising, on its side which faces the magazine, a motor having a drive shaft and a star-shaped part and a latching plate mounted thereon, the latching plate having at least one nub which, after insertion of the star-shaped part into a star-shaped cutout in the suction pipette and after rotation of the star-shaped part and the latching plate into a locking position, engages a notch which is situated in a surface of the suction pipette which faces the fitting head, and wherein the nub, on insertion of a suction pipette into the magazine can be moved out of the notch, further wherein the magazine has on a side facing the fitting head a sliding ring which is arranged in a rotationally fixed manner in the magazine and into which the suction pipette can be inserted so that an outer edge portion of latching plate comes to rest on the sliding ring at a point where it is raised away from the star-shaped part so that the nub is situated above that surface of the suction pipette which faces the fitting head, and after rotation of the star-shaped part and the latching plate into a locking position and removal of the suction pipette from the sliding ring, said nub engages the notch when the latching plate is relaxed, and when the star-shaped part enters into the sliding ring is raised by prestressing and raising the latching plate upward out of the notch.

2. The device according to claim 1, wherein the sliding ring further comprises a lower flange and an upper flange and the magazine is formed with a step on its side facing the fitting head, the step supports the lower flange of the sliding ring and the upper flange rests on an edge region of a cutout in the magazine, said cutout accommodating the sliding ring.

3. The device according to claim 1, wherein the sliding ring consists of a plastic material having a low coefficient of friction.

4. The device according to claim 1, wherein the latching plate is coated with a material having a low coefficient of friction said coating being present at least where said plate contacts the sliding ring.

5. The device according to claim 1, wherein the latching plate consists of spring steel.

6. The device according to claim 1, wherein the sliding ring is fastened to the magazine by at least one retaining spring.

7. The device according to claim 6, wherein the retaining spring has a substantially U-shape configuration, a first leg of the "U" is attached to the magazine and extends radially outward in a radially extending incision formed in the magazine and merges into a second leg of the "U" which extends radially inwardly above the first leg in said incision, and wherein a free end portion of the second leg is guided through a cutout in the sliding ring.

8. The device according to claim 7, wherein the inside of the free end of the second leg of the spring projects over the sliding ring, and on insertion of the suction pipette into the magazine and its removal therefrom, can be passed through an incision in the suction pipette.

9. The device according to claim 6, further comprising two opposed retaining springs.

10. The device according to claim 1, wherein a bayonet type lock secures the star-shaped part to the suction pipette and the pipette has wall parts which protrude radially inwardly above the star-shaped cutout and under which projections of the star-shaped part pass on rotation of the star-shaped part into a locking position, and wherein the notch is situated on a surface of a wall part which faces the fitting head.

11. The device according to claim 10, wherein the suction pipette has a stop restricting the rotational movement of the star-shaped part and securing the locking position.

12. The device according to claim 10, wherein the suction pipette has an added stop which restricts the rotational movement of the star-shaped part when not in a locking position, and into a position in which the retaining springs are aligned with respect to slots in the suction pipette.

* * * * *